United States Patent [19]

Meringola

[11] Patent Number: 4,966,595
[45] Date of Patent: Oct. 30, 1990

[54] SURGICAL SPONGE ASSEMBLY

[75] Inventor: Joseph Meringola, Farmingdale, N.Y.

[73] Assignee: Medical Action Industries, Inc., Farmingdale, N.Y.

[21] Appl. No.: 241,032

[22] Filed: Sep. 6, 1988

[51] Int. Cl.$^5$ .............................................. A61F 13/00
[52] U.S. Cl. .................................... 604/393; 206/63.3
[58] Field of Search ...................... 604/358, 386, 393; 128/201, 334; 24/563, 543; 224/42.45 A; 206/63.3

[56] References Cited

U.S. PATENT DOCUMENTS

| | | | |
|---|---|---|---|
| 2,542,369 | 2/1951 | Steendahl | 224/42.45 A |
| 3,515,129 | 12/1967 | Truhan | 128/20 |
| 4,415,089 | 11/1983 | Ruffa | 206/63.3 |
| 4,477,256 | 10/1984 | Hirsch | 604/358 |
| 4,673,153 | 6/1967 | Hiltey et al. | 24/563 |

Primary Examiner—Richard J. Apley
Assistant Examiner—Rachel M. Healey
Attorney, Agent, or Firm—Bauer & Schaffer

[57] ABSTRACT

There is disclosed a surgical sponge assembly which includes in combustion, a plurality of multi-layer, gauze fabric bodies, each having attached thereto along one side thereof, a twill strip of greater length than the length of the gauze body and a slotted strip having a plurality of slots equal in number to the number of twill strips and in each of which slots, the unattached end of each twill strip is removeably held.

4 Claims, 1 Drawing Sheet

SURGICAL SPONGE ASSEMBLY

BACKGROUND OF THE INVENTION

This invention relates to surgical sponges. Surgical sponges are known and have for many years been employed in hospitals where surgical medicine is practiced to soak up and clean away blood, as well as other debris, in a surgical cavity made in the body in order to accomplish a given surgical purpose.

Generally, surgical sponges such as laporatomy sponges are simply multi-layered gauze squares having a high absorption capacity and which are of a conventional size so that they may be easily used for insertion and withdrawal from the surgical cavity, once they have accomplished their purpose. They are usually square shaped and have dimensions of 3×3 inches and comprise 3 to 5 layers of absorbent gauze fabric which has been, or will be appropriately sterilized before actual use.

In operating room procedures, when surgery is being performed, it is the general practice to carefully count the number of sponges inserted in a body cavity and then to count the same upon removal and prior to disposal. This is sometimes difficult after the sponges become wet as they tend to cling to others, as well as to other fabric material in the operating room. In the event that the input count and withdrawal count do not agree, emergency procedures are initiated to locate the missing sponge or sponges. The cavity, in accordance with established procedures, is not to be closed until all missing sponges are accounted for. For this purpose, a special nurse is required, whose sole duty it is to insure that the number of sponges are accounted for before, during and after the surgical procedure.

Even if the input and withdrawal counts agree, one or more sponges may remain in the body of a patient, or by careless tossing or disposal, fall on the floor or in a wrong tray and may be considered "lost". These can not only cause detrimental effect to the patient ranging from mild to serious discomfort, but also such unaccounted for sponges may cause serious complications necessitating further surgery on the patient, as well as placing the hospital and surgical staff under probable liability for negligent practice. Since the presence of such sponges in the body of a patient, are difficult or impossible to detect by post-surgery x-rays, there exists, therefore, a need for insuring an accurate count in a simple effective and fast way. The present invention fulfills such a need.

BRIEF STATEMENT OF THE INVENTION

In accordance with the present invention, there is provided a surgical sponge assembly comprising in combination, a plurality of multi-layer sponges, each body having attached thereto along one side thereof, a twill strip and a holder provided with a specifically predetermined number of slots equal in number to the number of twill strips and in each of which slots, the unattached end of a respective one of twill strip is removably held. The sterilized sponges can be attached to the holder, used and then replaced on the holder so that even heavily saturated sponges are separately and individually maintained.

In this way, the initial number of sterilized sponges are instantly discernible and similarly the number of used or soiled sponges, can be readily and easily "racked" so that they too can be accurately counted.

BRIEF DESCRIPTION OF THE DRAWINGS

In order to describe the present invention more fully, reference is directed to the accompanying drawing which is to be taken in conjunction with the following detailed description thereof and in which drawing.

DESCRIPTION OF THE PREFERRED EMBODIMENTS

Figure 1:
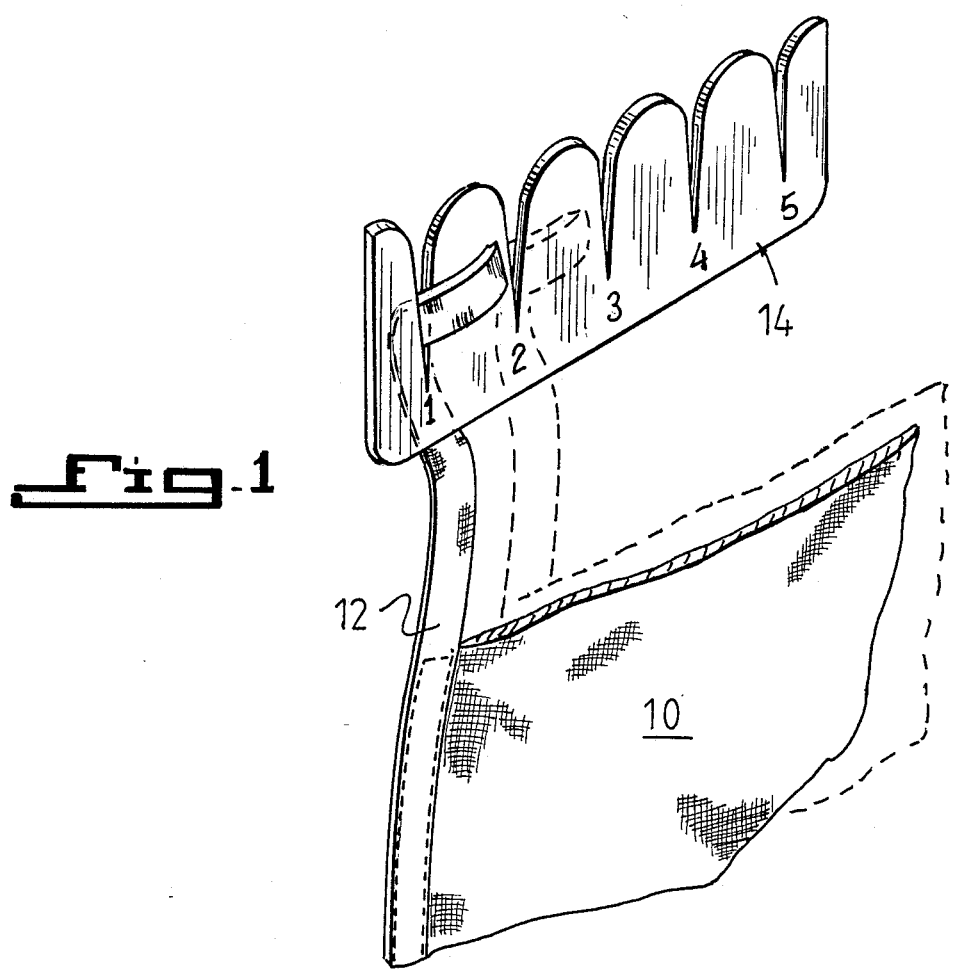
FIG. 1 is a perspective view of a surgical sponge assembly according to the present invention, showing a plurality of gauze fabric bodies, each provided with a twill strip and a slotted holder provided with a plurality of slots in each of which slot, the unattached end of each twill strip is removeably held.
Figure 2:
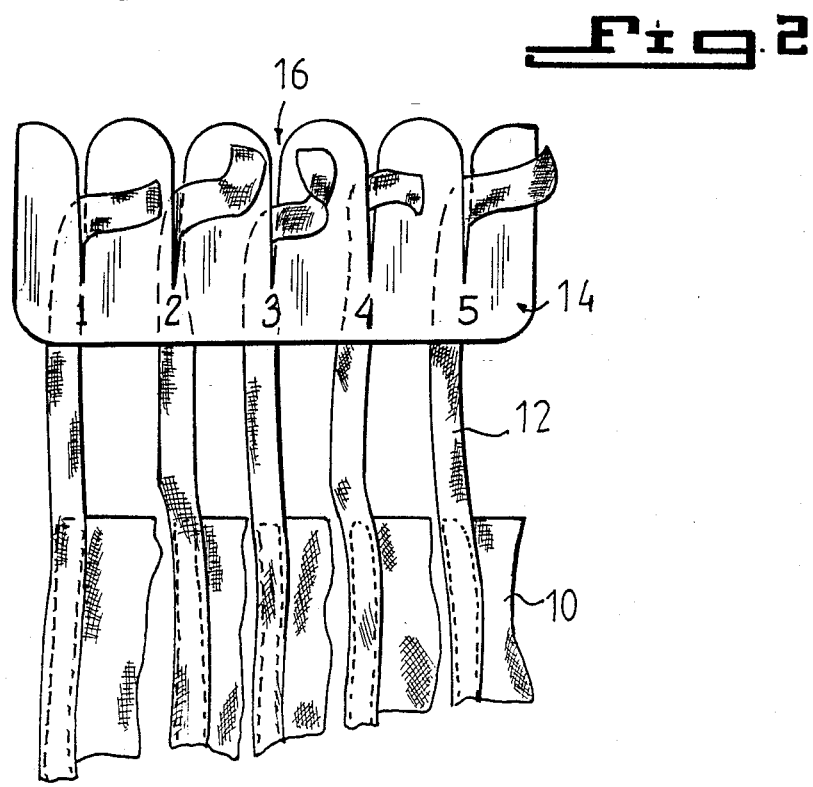
FIG. 2 is a front elevational view of the assembly seen in FIG. 1.

Referring now to FIG. 1, the assembly shown provides a plurality of multi-layered square shaped gauze fabric sponge bodies 10, each having attached thereto along one side thereof, hang tag or a twill strip 12. The strips 12 have a length greater than the length of the respective bodies so that the sponge can be easily handled by the medical personnel without contaminating the sponge, or being contaminated themselves through contact with the dirty sponge. The sponge assembly includes a holder or rack 14 provided with a plurality of slots 16 of a predetermined number. The number of sponge 10 employed with the rack will, of course, equal the number of slots 16, so that each sponge 10 will have its corresponding slot into which its respective twill strip 12 is insertable.

The twill strip 12 attached to a typical sponge body 10 is preferably made from any known type of woven fabric, and is dense enough to be relatively easy to be located by post-surgery x-rays. An inner portion made of plastic material, such as polyethylene or other suitable plastic, for example, which is easily detectable by post-surgery x-ray procedures may also be used. The twill strip may be attached to the gauze body in any conventional manner.

The slotted rack 14 may be made from any suitable material, such as good quality paperboard plastic and the like. So long as it has strength enough to withstand sterilization procedures and wetting by body fluids and the like. Preferably the rack is made of plastic, such as polyethylene.

It has become conventional to package groups of five sponges in paper or plastic sterilized wrappers, for ease in handling, as well as counting. Thus, the present invention provides a rack 14 with 5 slots, conveniently numbered 1-5 so that it can be assembled with a like member of sponges 10. However, should requirements dictate, it may be made with another number of slots to accommodate a lesser or greater number of sponges.

Thus, with the present invention, one has a correct count at all times simply by completing the re-racking after use with substantially no chance at a miscount occurring. In the event of the unlikely occurrance of an undetected error and the leaving of a sponge in the body, it is likely to be easily detected by the nurse since the sponge will be visibly absent on the last of the racks to be filled.

In practical use, sterilized packages of sponges, attached to the rack by insertion of the twill strip into a respective one of the slots as indicated above, is delivered to the operating room, where the special nurse removes the contents. The exact number of sponge will be evident immediately by visually noting that each slot has attached thereto a twill strip. As the soiled sponges are retrieved by the nurse, she remounts them by the twill strip in a slot on an otherwise empty rack. Once all the slots are filled with sponges, the entire assembly of dirty sponges can be discarded. Discarding therefore, provides in itself, an easy count by the number of racks.

It will be appreciated, that during even the most routine surgery, several hundred sponges may be used and soiled, each of which must be accounted for. Thus, the inventive assembly is advantageous in subatantially eliminating completely, miscounts and at the same time, providing simple means for discharging soiled sponges.

Various modifications and changes have been discussed and others will be apparent to those skilled in the art. Accordingly, it is intended that the present invention be taken as illustrative rather than restrictive of the scope of the present invention.

What is claimed is:

1. A surgical sponge assembly comprising in combination, a plurality of sponges, each having attached thereto along one side thereof a twill strip, and a holder provided with a plurality of slots equal in number to the sponges, the twill strip of each individual sponge being attached in a corresponding slot of said holder, whereby the number of such sponges, as well as their individuality are readily visible.

2. The assembly according to claim 1, wherein the holder is made of plastic.

3. The assembly according to claim 2, wherein the holder is made of polyethylene.

4. The surgical sponge assembly according to claim 1, wherein each twill strip has an inner portion which is made of plastic.

* * * * *